(12) United States Patent
Humphrey et al.

(10) Patent No.: US 9,915,590 B1
(45) Date of Patent: Mar. 13, 2018

(54) SYSTEM AND METHODS FOR MAINTAINING CONSTANT AIRFLOW AND EFFICIENCY WHILE TUNING SAMPLING FLOW

(71) Applicant: HOLLISON, LLC, Owensboro, KY (US)

(72) Inventors: Kevin Humphrey, Utica, KY (US); Anthony Bashall, Concord, MA (US); Roger Dame, Owensboro, KY (US); David Humphrey, Calhoun, KY (US)

(73) Assignee: HOLLISON, LLC, Owensboro, KY (US)

( * ) Notice: Subject to any disclaimer, the term of this patent is extended or adjusted under 35 U.S.C. 154(b) by 0 days.

(21) Appl. No.: 15/229,846

(22) Filed: Aug. 5, 2016

Related U.S. Application Data

(60) Provisional application No. 62/282,637, filed on Aug. 7, 2015.

(51) Int. Cl.
G01N 3/02 (2006.01)
G01N 1/04 (2006.01)
G01N 33/02 (2006.01)

(52) U.S. Cl.
CPC ............. G01N 1/04 (2013.01); G01N 33/02 (2013.01)

(58) Field of Classification Search
CPC ............. G01N 1/2211; G01N 33/227; G01N 2001/022; G01N 1/24; G01N 2001/028; G01N 2001/2223; G01N 15/065; G01N 2001/2264; G01N 1/2252; B07B 7/086; B07B 11/06; B01D 47/02; B01D 45/16; F02D 41/1466; F01N 11/00; B03C 3/017; B03C 1/288; B03C 1/30; B03C 1/0335; B04C 11/00; B04C 2009/001; B04C 9/00; B04C 2009/004
USPC ... 73/23.31, 863.61, 863.03, 863.12, 864.71, 73/863, 28.01, 28.05, 864.34
See application file for complete search history.

(56) References Cited

U.S. PATENT DOCUMENTS

| 4,513,830 A * | 4/1985 | Persbeck ............... G01G 11/14 119/14.17 |
| 4,900,445 A | 2/1990 | Flanigan et al. |
| 5,062,870 A | 11/1991 | Dyson |
| 5,121,638 A * | 6/1992 | Gmur ....................... G01F 1/76 177/114 |
| 6,355,178 B1 | 3/2002 | Couture et al. |
| 6,843,103 B2 * | 1/2005 | Aguilera .................. G01F 1/74 73/28.01 |

(Continued)

FOREIGN PATENT DOCUMENTS

GB 2254024 A 9/1992

Primary Examiner — Harshad R Patel
Assistant Examiner — Brandi Hopkins
(74) Attorney, Agent, or Firm — Wyatt, Tarrant & Combs, LLP; Stephen C. Hall; Max E. Bridges

(57) ABSTRACT

In a material sample separation and collection system, a sample is obtained by airflow separation. The system and attendant methods collect a complete sample over a defined period of time by modulating one or more pressure balancing valves, thus allowing for a variable flow rate of materials through the system even while the fan or other source of airflow operates at constant speed. The sampling rate, which is based on how quickly or slowly materials enter and pass through the system and into a collection vessel, is automatically modulated in real time based on sensor data.

12 Claims, 3 Drawing Sheets

(56) References Cited

U.S. PATENT DOCUMENTS

Figure 1:
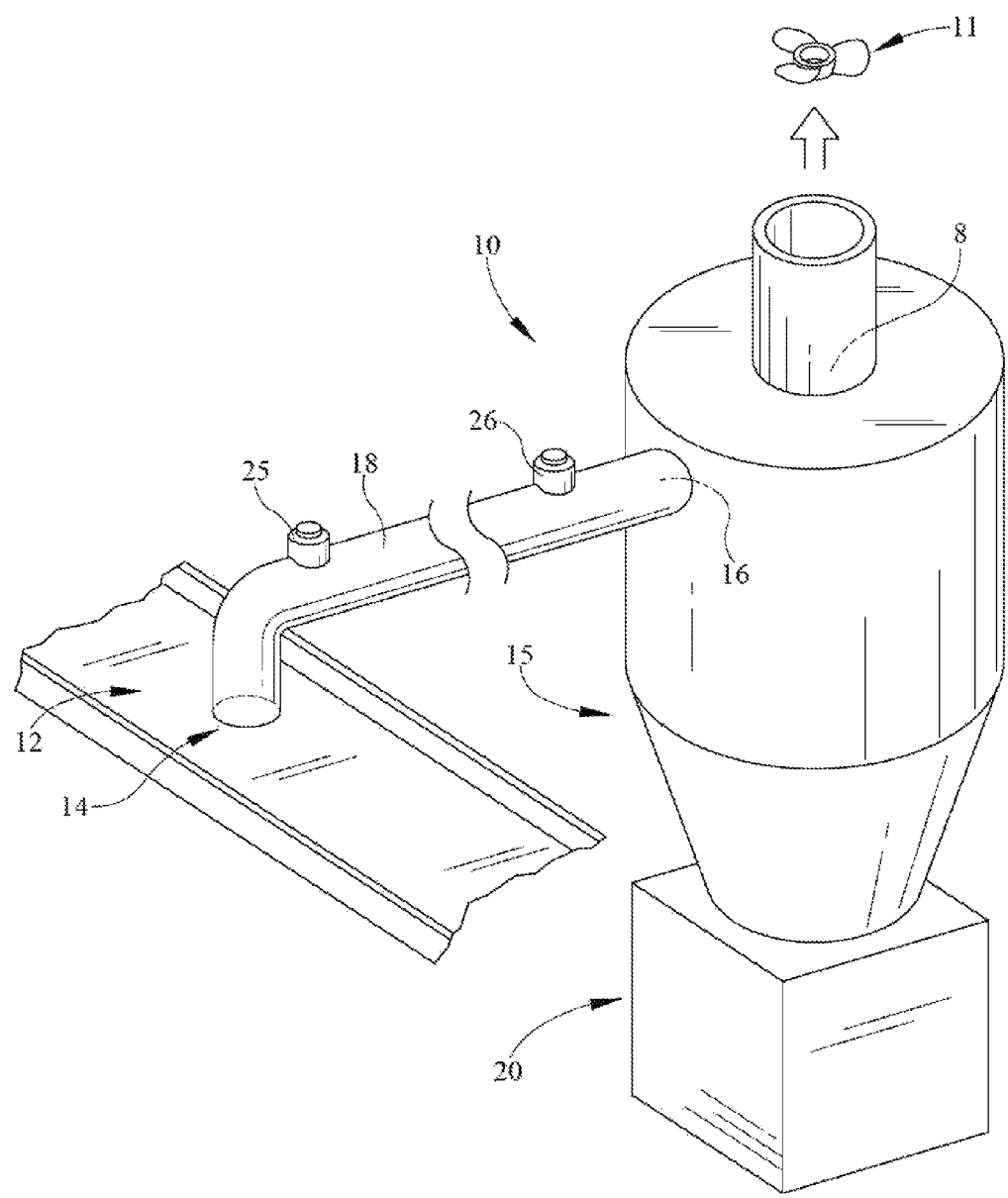

| | | |
|---|---|---|
| 7,108,138 B2 | 9/2006 | Simpson |
| 7,281,440 B2 | 10/2007 | Graze, Jr. et al. |
| 7,347,112 B2 | 3/2008 | Kay |
| 7,647,811 B2 | 1/2010 | Wei et al. |
| 7,964,018 B2 * | 6/2011 | Kang .................... B01D 45/12 95/13 |
| 8,167,986 B2 | 5/2012 | Schneider et al. |
| 8,188,874 B2 | 5/2012 | Calio |
| 8,323,383 B2 | 12/2012 | Evans et al. |
| 8,875,589 B1 | 11/2014 | Mancinho et al. |
| 9,028,758 B2 | 5/2015 | Keinan et al. |
| 9,335,236 B2 | 5/2016 | Bry et al. |
| 2011/0159596 A1 * | 6/2011 | Keinan ................ G01N 1/2211 436/52 |
| 2015/0183003 A1 | 7/2015 | Humphrey et al. |

\* cited by examiner

SYSTEM AND METHODS FOR MAINTAINING CONSTANT AIRFLOW AND EFFICIENCY WHILE TUNING SAMPLING FLOW

CROSS REFERENCE TO RELATED U.S. APPLICATION

This application claims the benefit of priority to U.S. Provisional Application No. 62/282,637, which was filed on Aug. 7, 2015, the contents of which are incorporated herein by reference.

FIELD OF INVENTION

Embodiments described herein relate to taking samples of bulk materials and other kinds of materials as they pass by a sampling point, so that the samples can be tested. There are provided systems, methods, and processes for maintaining constant rate flow, allowing for optimal separator performance, while tuning the sampling rate flow into a collection vessel receiving sample particles and materials.

BACKGROUND

In commerce, many goods are sold as bulk materials. The term "bulk materials" refers to items obtained, transported, used, stored, or handled in a group, non-limiting examples of which include grain, wheat, vegetables, tea, spices, flavorings, peanuts, coffee beans, soybeans, and other agricultural products; manufactured food products (including human food and pet food products); and pharmaceutical or other health products such as multivitamins and supplements. Each example is an item that can be broken down into individual units and grouped with numerous others of its kind for packaging or shipment, or grouped with others of its kind and used as food ingredients. In a production plant, bulk and other materials are frequently sent along a conveyor as part of the production process. Often, the bulk materials are in the form of particulates. In some instances, the materials which are sampled are liquid, whereby a portion of the liquid is separated and transported into the collection device.

There is a need to sample bulk and other materials to determine if they contain any matter that causes injury, disease, or irritation if inhaled or ingested by a person or absorbed through the skin, or matter that creates a risk of combustion or explosion, either by itself or in contact with other matter. Such matter is characterized in different ways, and depending on its nature may be referred to variously as contaminants, adulterants, pathogens, viruses, bacteria, microorganisms, fungi, toxins, toxic chemicals, and pollutants. For brevity, such examples of matter set forth in this paragraph are referred to herein as "contaminants."

Alternatively, a need exists to sample materials to determine if they contain matter that is desirable and beneficial, i.e., which is supposed to be present. Such substances include, again by way of illustration only, an additive used to enhance a manufacturing process related to a particular commodity; or matter incorporated with a particular commodity providing beneficial, nutritional, or therapeutic effects, such as proteins, nanoparticles, and additives. For brevity, all such substances contemplated by this paragraph are referred to, individually and collectively, as "additives."

In the past, various attempts have been made to sample materials, for the purpose of testing to see if contaminants or additives are present in the bulk materials. In some instances, the materials are related to food, while in other contexts this sampling has been performed on non-food bulk materials. The present embodiments are not limited to the type of materials (bulk or otherwise) which they are practiced upon.

In this sense, sampling the bulk materials, or "taking a sample," involves separating a large quantity of bulk materials into a very small portion that is taken out of production and used for sampling, from the remainder of the bulk materials. Airflow separators are used in many applications to separate particulate matter as a means of collecting a sample, where separation occurs based on differences in size or density (or both) of particles making up the bulk materials. Cyclonic separators, also referred to as cyclones, are a type of airflow separator, having a geometry which facilitates a cyclonic airflow within the chamber as the airflow is drawn into and through it. Other airflow separators produce different kinds of air movement, including but not limited to axial flow, laminar flow, and turbulent flow. Although the term cyclonic separator is used somewhat more frequently herein than some other types of airflow separators, embodiments are not limited to cyclonic separators.

Airflow separators are usually operated by a fan run at constant speed that draws air into and through the device, as running them at constant speed is important for maintaining consistency of performance. As air enters and travels through the device, by the action of the fan, the resulting airflow transports some of the particles away from the sampling point and into the cyclone via a conduit. Generally, cyclonic separators operate based on a precise flow determined by the physical design characteristics of the cyclone and the requirements for sample separation and collection, in order to maintain a constant and precise flow of air and matter through the cyclone that increases sampling efficiency.

Conventional airflow separators are known generally to those skilled in the art. These include, but are not limited to, collectors, separators, wetted wall cyclones, and multi-stage configurations, all of which transport material under a flow of air or gas. Such airflow separators handle a wide range of products, including but not limited to particles, aerosolized particles, liquids, aerosolized liquids, biological material, and metals, any of which can be dispersed in air or other gases.

In most cases when contaminants are present in bulk materials, the contamination is localized, rather than diffuse, i.e., spread throughout the entirety of the bulk materials. Thus, although various approaches have been tried before with respect to sampling to determine contamination, the results have been poor because usually the approach involves "grab sampling" or some other technique that obtains a sample only at intervals. In some cases, the protocol calls for a person to manually obtain a sample at some predetermined interval. Other times, the sampling process is automated so that a machine obtains the sample, for example by pneumatic force or suction that redirects a portion of bulk or other materials moving along a conveyor or stored in a bin, or otherwise going through production steps. Again, though, conventional sampling performed through automation is limited just like manual sampling, in that it is done at discrete intervals. Also, sample volumes collected through automation are usually fixed and, therefore, not subject to adjustment. Consequently, localized contamination is detected only if the contamination passes the sampling point at the precise interval when the sample is taken.

Although airflow separators are known, problems and limitations are still encountered in their use. For example, the performance of cyclonic separators depends on maintaining a precise and constant flow of air and matter through the device at a preset, constant fan speed. However, these constants might not be compatible with the sampling flow requirements of a particular operation, in which sampling rate may be lower than the optimum cyclone flow. Stated differently, one operation might want to fill a sampling vessel every hour, while another might only fill the sampling vessel once or twice during an eight hour shift. Consequently, changing (raising or lowering) the total flow within this type of airflow separator to an optimum value for sampling might negatively impact the cyclonic efficiency and performance, for example if the fan speed were turned lower to reduce the rate at which sample is being collected. The problem is that when one changes flow through the total system by varying fan speed, or changing the restriction of air movement, for example, it can have negative impact on the overall performance of the cyclone.

Accordingly, there is significant need for continuous automated sampling, where the sampling rate can be varied even though the fan speed remains constant.

SUMMARY OF EMBODIMENTS

Embodiments are provided that regulate the volumetric flow of sampled material that enters and passes through a sampling and collection system. In one embodiment, sampled material from a sampling point enters a cyclonic separator, a.k.a. cyclone, where the sampled materials are collected for further study and testing. Although frequent reference is made herein to a cyclonic separator, other kinds of airflow separators are within the scope of present embodiments, e.g., those generating axial, laminar, and turbulent airflow patterns to name several.

One advantage of the present embodiments is the ability to vary the volumetric collection of sampled material, without having to change the total flow through the airflow separator. In some embodiments, the practice allows one to sample fine particulate material as well as smaller particulates contained in their interstitial headspace (e.g. flour, masa, fine particulates, etc.). Other utilizations include providing a particulate sample in a liquid carrier fluid by use of a wetted wall cyclone. Still other applications are within the scope of present embodiments, which provide for regulation of solid bulk material being collected as a sample by use of a cyclone or other airflow separator. All such uses share the common feature that bulk volumetric flow is adjusted by modulating one or more pressure balancing valves (a.k.a. "valves"). In some embodiments, these valves are positioned along a conduit that serves as a sampling tube, positioned between a sampling point and the cyclonic separator. Accordingly, the opening (partial or full) of one or more valves creates a pressure drop that draws air into the valve(s) from positions distal to the sampling point, which changes the sample rate.

In this way, a desired amount of sample material collected can be predetermined, and the rate of collection (i.e., the period of time over which a sample collection vessel will become substantially filled) can be set. In some embodiments, a control loop based on sensor feedback is established between the one or more valves responding to sensor inputs provides a control loop that affects the sampling rate as a desired amount of sample material is collected over time.

Accordingly, current embodiments provide for systems, and like methods, for allowing the flow of air and matter through the airflow separator to be maintained as a constant, while also being able to adjust the sampling rate using one flow source (for example, the aforementioned fan) to draw air into and through the entire sampling system. The cyclones themselves which are suitable for use with current embodiments are commonly used by persons of ordinary skill in using them for the separation of matter, but the arrangement of pressure balancing valves as part of this overall system is unique and provides a solution to previously recognized problems associated with variable sampling rate under constant fan speed. In connection with the present embodiments, it will be appreciated that there are a number of possible candidates that can be used in place of a fan, including impellers, pumps, compressors, turbines, and other similar items for drawing a flow of air, as known in the art, all of which are associated with continuous airflow. With the present embodiments, as airflow is drawn into and through the system, including the conduit and the cyclone itself, certain adjustments for controlling the sampling rate are achieved by the use of one or more pressure balancing valves positioned along the sampling conduit, and otherwise physically separated from the conduit inlet. Alternatively, one or more valves can be positioned on the airflow separator outlet. In some embodiments, one or more valves is placed "upstream" of the separator device, i.e., between the sampling point and the airflow separator chamber. One or more pressure balancing valves are then modulated by actuating the position of the valve(s) between fully opened, partially opened, and fully closed.

To accommodate the interests of having an optimum flow rate with a variable sampling rate, one or more valves is modulated between fully opened, partially opened, and closed. Modulation is based on a number of factors, including, but not limited to, sample size, sample density, rate of movement of bulk materials at the sampling point, sampling conduit diameter, moisture content of the bulk materials, rheology of the bulk materials, desired sampling rate, desired sample collection amount, and dispersion into a fluid matrix, among other factors.

Present embodiments include those using one or more sensors that track the entry of sample material into a collection vessel that is part of, otherwise connected to, the airflow separator. Based on sensor inputs, one or more pressure balancing valves are adjusted, preferably automatically, by use of an algorithm driving a feedback loop to influence the operational characteristics of the system acting under a constant rate of flow of air and matter, and to achieve the required sample flow rate.

FIGURES

The drawings, schematics, figures, and descriptions provided are to be understood as illustrative, and the scope of the embodiments are not limited to the precise arrangements or scales as shown in these Figures.

FIG. 1 is a perspective view of parts of a material separation and sampling system that are involved with separating and collecting a sample, according to multiple embodiments and alternatives.

FIG. 2 is a schematic of a material separation and sampling system that illustrates a control loop for modulating one or more valves to influence sampling rate, in addition to other system components that are involved with physically separating and collecting a sample, according to multiple embodiments and alternatives.

Figure 3:
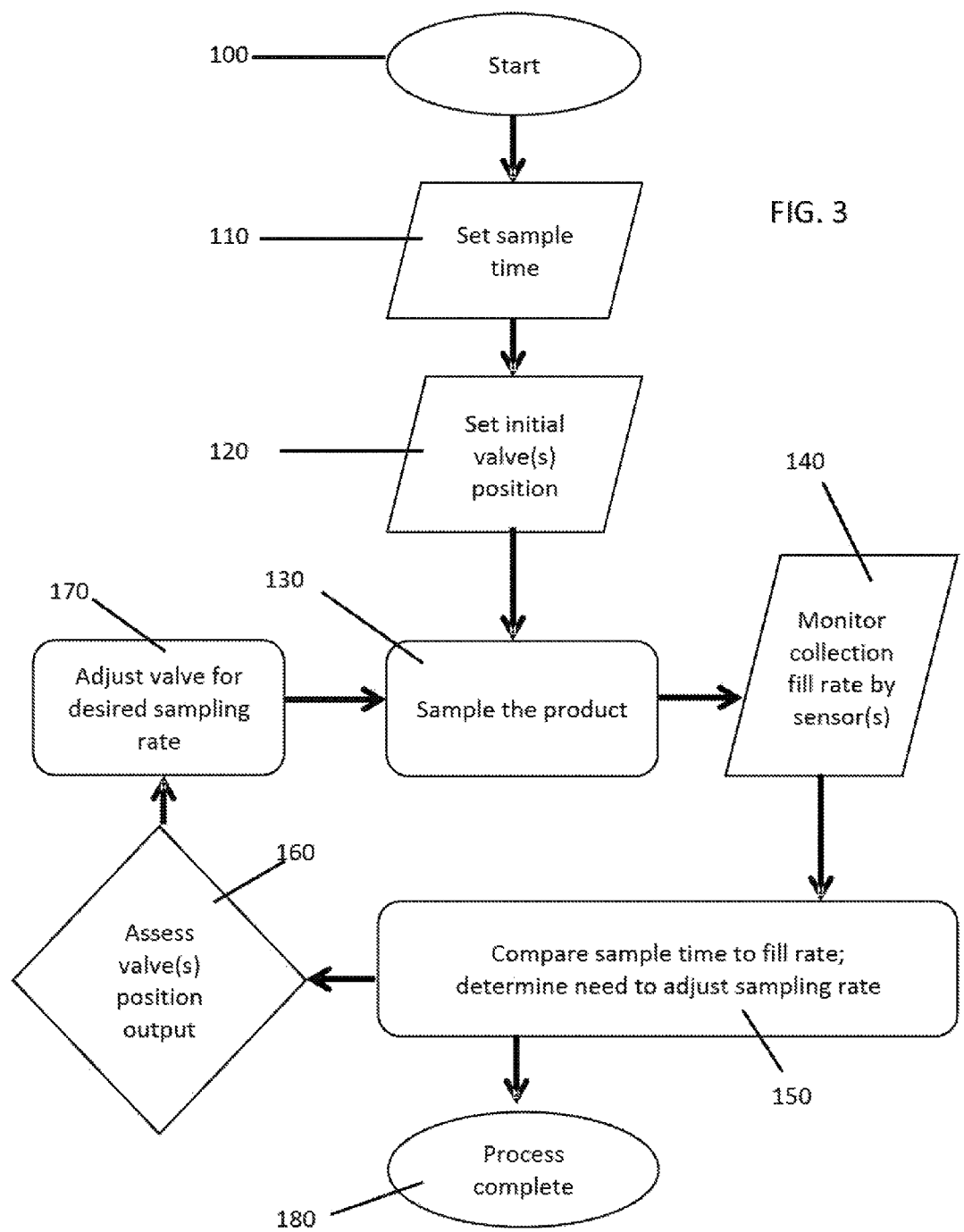

FIG. 3 is a flow chart depicting an algorithm for modulating one or more valves to influence sampling rate, according to multiple embodiments and alternatives.

MULTIPLE EMBODIMENTS AND ALTERNATIVES

The practice of present embodiments provides for separation of solid and liquid materials at a sampling point where the force creating airflow through the system is fixed and constant, while the flow rate of materials into and through the system is variable. Accordingly, the sampling rate, which is based on how quickly or slowly materials enter and pass through the system and into a collection vessel, is modulated automatically based on real time sensor data. After the separation occurs at the sampling point, the result is that some materials from the sampling point are transported through the inventive system and are collected for sampling. It will be appreciated that the present system 10 is useful for sampling and collecting many types of materials, both food and non-edible, as well as bulk materials and liquids, such that the rate of sampling and the volume sampled over time are variable.

FIG. 1 is a perspective view of an exemplary material sample separation and collection system 10. As shown, such an embodiment comprises at least one airflow separator 15 arranged for fluid communication with a sampling point 12. For illustrative purposes, the figures depict airflow separator 15 as a cyclone. The sampling point 12 may be positioned where a user desires along a conveyor system that is set up to transport the materials during normal production. Conduit 18 provides fluid communication between airflow separator 15 and sampling point 12. In some embodiments, an airflow separator outlet 8 of airflow separator 15 communicates with a fan 11 or other similar component that draws an air stream of flowing air into and through conduit 18, proceeding to airflow separator 15. In this manner, sampled material enters conduit 18 via conduit inlet 14, and it travels through conduit 18 until it enters through an airflow separator inlet 16 proceeding into airflow separator 15. In some embodiments, the airflow separator 15 is configured so collected sample material drops into collection vessel 20 under gravity. It will be appreciated that other impetuses can be used to urge the collected sample material into collection vessel 20 after entering airflow separator 15, such as but not limited to under pneumatic force or suction. In addition, FIG. 1 illustrates one or more valves (labeled as 25 and 26) positioned along conduit 18. When opened, partially or fully, these valves provide communication between conduit 18 with the ambient environment away from the sampling point 12, and the system will draw in a greater proportion of air than product because one or more opened valves that feed into conduit 18 is not near the sampling point. In some embodiments, one or more valves is located upstream of the cyclone, as shown in the accompanying drawings. Alternatively, one or more valves is located downstream of the cyclone, for example at the cyclone outlet where the drawn airflow leaves the cyclone. Alternatively, one or more valves is located upstream and one or more valves is located downstream of the cyclone. Embodiments are not limited by the precise location of one or more valves.

Figure 2:
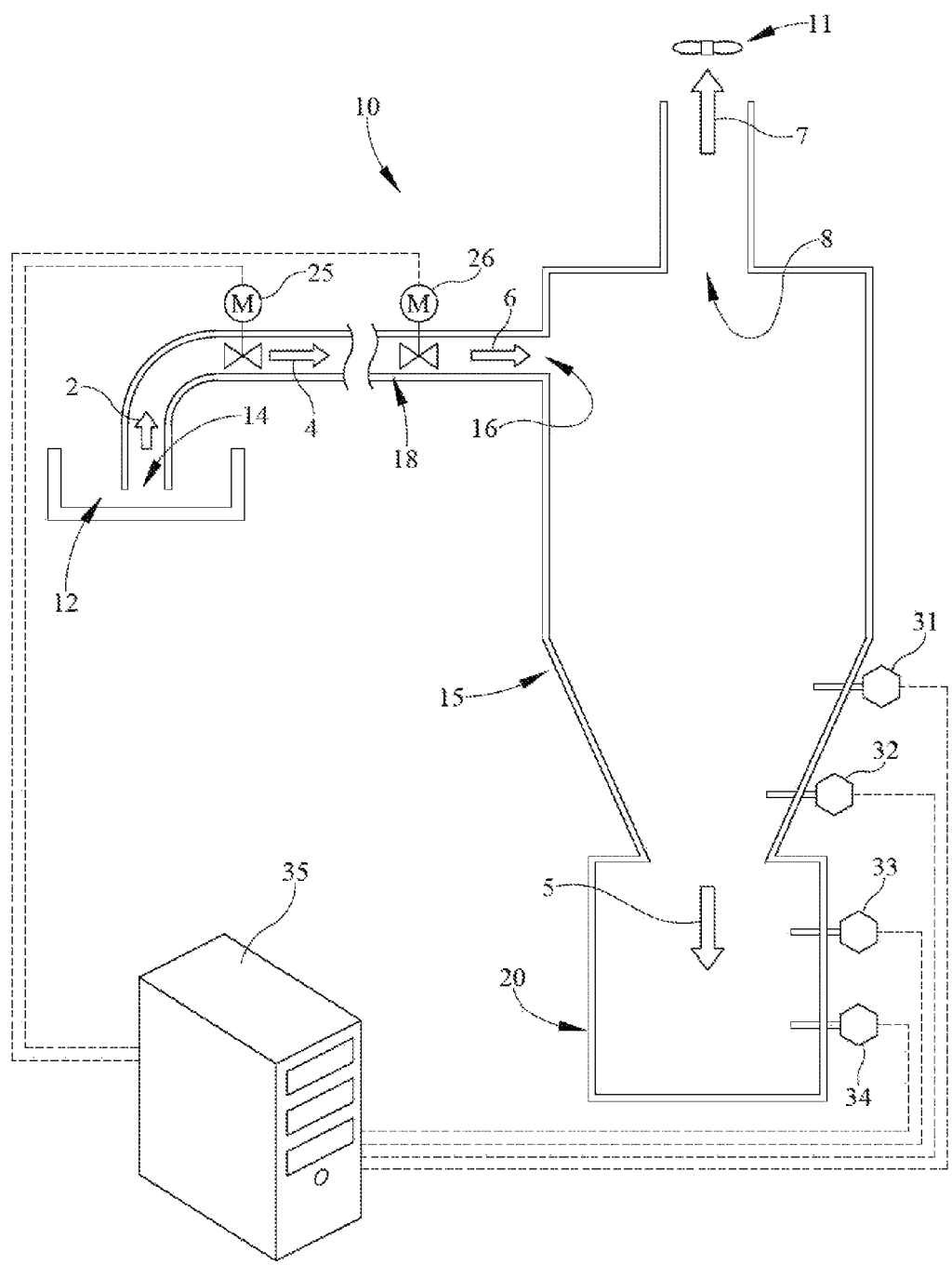

FIG. 2 depicts that, in broad terms, fan 11 generates a vacuum in a direction indicated by arrow 7 that creates a force sufficient to draw airflow into the system at several positions. In some embodiments, airflow separator 15 is a cyclone comprising a substantially closed chamber, the geometry of which facilitates a cyclonic airflow within the chamber as the airflow is drawn into and through it by fan 11. As shown in FIG. 2, fan 11 communicates with the airflow separator 15 and conduit 18, for example as shown here via airflow separator outlet 8, airflow separator inlet 16 and conduit inlet 14. The force drawn by the fan creates airflow into conduit 18 via inlet 14 as noted by directional arrow 2. As air rushes into the conduit 18, it also separates some of the material as it passes the sampling point by drawing it into the conduit inlet 14. Both air and matter from the sampling point continue to travel through conduit 18 as noted by directional arrow 4, before exiting the conduit at airflow separator inlet 16 as noted by directional arrow 6. Once inside airflow separator 15, air will tend to escape the cyclone through outlet 8 as a result of the force drawn by fan 11, while heavier solid or liquid matter tends to fall out and be captured in collection vessel 20 is indicated by directional arrow 5.

Alternative embodiments include those where the collection of particulate sample material is facilitated by introducing a carrier fluid into the separator. The carrier fluid may be introduced from a reservoir, such as through a separate port (not shown), provide a liquid-borne sample by use of a wetted wall cyclone because the carrier fluid urges the collected sample into the collection vessel.

FIG. 2 also illustrates the control loop components for modulating valve positioning. One or more sensors (here, labeled as 31-34) are positioned to sense changing conditions inside collection vessel 20. For automatic operation of the system, the one or more sensors detect various characteristics as the collection vessel fills, and provide a signal to processor 35, which in turn makes adjustments based on the requirements of an algorithm that modulates the opened/closed (or, partially opened/closed) status of one or more valves, 25, 26.

Accordingly, in some embodiments, total system flow is provided by a single source, for example fan 11, which is controlled at a constant rate of speed to maintain the required performance characteristics of the airflow separator 15, whereby sampling rate is modulated by the positioning and opened/closed status of the one or more pressure balancing valves. These valves are positioned along the system (e.g. integral with conduit 18) to provide communication with the ambient atmosphere away from the sampling point. When one or more valves is open, the fan pulls a proportionally larger amount of ambient air (and, therefore, less particulate or other material at sampling point 12). More air entering the system through the valve(s)—because one or more is opened as opposed to closed, or opened wider as opposed to more narrowly opened—means less sample is collected over a unit of time. The reverse is also true, in that closing one or more valves, fully or partially, will increase the rate of sample collection. Accordingly, each of one or more valves 25, 26 (as shown) is modulated. In turn, this causes the amount of sampled material separated from bulk or other materials moving past the sampling point to be adjusted to the required value, which is based on a desired sampling rate, and this occurs without altering the total flow of air through cyclone 15. Thus, when collecting a sample, any particulates meeting the determined size, density, and other characteristics needed for the sample are drawn through the sampling conduit 18, enter the cyclone 15, and are retained in the collection vessel 20. In some embodiments, the sample is not collected from bulk materials, often containing particulates, but rather from a liquid. The principles of operation generally are the same, in that a portion of the liquid is separated at sampling point 12 due to the draw of the air stream and transported into conduit 18, but rheology factors come into play more than size and density factors.

The position of one or more valves 25, 26 is modulated automatically in response to real-time data associated with sensed conditions and collection fill rates within collection vessel 20. Over the course of a sampling run, the system modulates the position of these valves from fully opened, to partially opened, to fully closed, in any order or sequence that meets the programmed sampling rate. As desired by a user, many different types of valves can be employed that are actuated by a variety of mechanisms. Single or multi-port valves may be utilized operated on the basic principles of, but not limited to, a ball valve, butterfly valve, slide valve, plate (or knife) valve, clapper valve, diaphragm valve, pinch valve or choke valve. These valves may be actuated electrically (motor or stepper motor), electromechanically (solenoid) or pneumatically (gas or liquid). Actuation and valve operation may be binary (opened/closed), adjustable or infinitely variable driven by analog or digital signals. Multiple valves of the same or different types can be used which are actuated by the same or different mechanisms.

FIG. 3 is a representation of the system in operation. At step 100, the system is started prior to sampling by turning on or otherwise accessing a user interface (not shown) that allows for settings to be made. Sample time, at step 110, is one of the settings a user can input. The sample time correlates to the length of time a user wants to take in filling up collection vessel 20 with sampled material. In some instances, sample time might be set at one sample every hour. If the sample rate is meant to be slower, it might be one sample every shift, or one sample every four hours, as examples. The sample time is selected by the user. The user also sets the initial valve position at step 120. Generally, sample collection rate slows as more valves is open, or as open valves are opened wider. Step 130 is the point where sampling begins, as bulk material product approaches the sampling point. Rather than sampling intermittently, system 10 samples continuously and at a variable rate of sampling, and this occurs until step 180, when the process is complete. Likewise, the practice of system 10 and its attendant methods enables one to vary the volume of sampled material or product collected over time, rather than merely having fixed volumes collected at specific discrete times as with conventional practices. Generally, completion of the process at step 180 may coincide with a given lot or batch of bulk materials or liquid material that has moved along a conveyor, or otherwise past the sampling point.

In an exemplary operation, for illustrative purposes only, sample time is set for four hours. Once sampling begins, sampled products travels through conduit 18 with the air stream generated by fan 11, enters airflow separator 15, and begins dropping into collection vessel 20. The level of the sampled material in the collection vessel determines a collection fill rate, which is proportional to the sampling rate. The collection fill rate is monitored by sensors at step 140. In this way, system 10 tracks a duration of time elapsed since step 130 until the collection vessel is filled to a level sufficient to be detected by a first sensor 34. Then at step 150, the system includes a timing module executed by processor 35 to compare the amount of time elapsed from step 130 to the point at which sensor 34 senses that the sample has reached this particular level. With a four hour sample time as used for this exemplary operation, the system tracks the duration of time to fill to the level of sensor 34. In some embodiments, the sensors are positioned so that each one accounts for the same proportional level of filling. For example, if there are four sensors and a four hour sample time, the first sensor 34 is positioned to detect the point at which collection vessel 20 is one-quarter full, a second sensor 33 is positioned to detect when collection vessel 20 is half full, a third sensor 32 is positioned to detect when collection vessel 20 is three-quarters full, and a fourth sensor 31 is positioned to detect when collection vessel 20 is full.

In this way, an output of collected sample associated with valve position is assessed at step 160. If it took one hour before sensor 34 detected its portion of the sample filling the collection vessel, in a four-hour sample time in view of this exemplary sensor array, the system does not modulate the position of one or more valves. However, if the amount of time is different than one hour, modulation of valve positioning between fully opened, partially opened, and fully closed (in any sequence) occurs as noted at step 170 as the sampling continues. For example, if it took less than one hour to reach sensor 34 in this exemplary operation, the sampling rate is going faster than the four-hour setting. Thus, the modulation would then be to close one or more valves either fully or by degrees according to the variance that must be adjusted for. If more than one hour to reach this sensor, then sampling rate is slower. Thus, the modulation would be to open one or more valves either fully or by degrees.

Accordingly, the system is programmed to undertake a predictive approach to valve settings as sampling continues, such that in the execution of Instructions, processor 35 causes the opening/closing (i.e., modulation between fully opened, partially opened, and fully closed in any sequence) of one or more valves, and sampling continues as per step 130. The modulation of valves 25, 26 at step 170 changes the sample collection rate during the period while sample increases in collection vessel 20 from the level of first sensor 34 to the level of second sensor 33. In this way, each point at which a particular sensor is triggered is associated with a defined portion of the volume making up collection vessel 20. In this way, the same pattern of steps 140, 150, 160, and 170 then occurs as sample fill reaches next levels that are sensed by each successive sensor (in this case, sensors 33, 32, and 31, respectively). The process is complete at step 180 when the collection vessel 20 is full. As desired, the system 10 is configured to automatically shut off when the collection vessel fills up, or to initiate an audible or visual alarm (or both) to indicate to a user that sampling is complete. Likewise, such alarms can be configured at intervals, such as when the sample material reaches the level of first sensor 34, and so forth. In some embodiments, collection vessel 20 and airflow separator 15 are separate structures in communication with the other such that collected sample flows into collection vessel 20. Alternatively, the two structures are integral, with the collection vessel 20 permanently joined to and otherwise part of the airflow separator 15. As well, embodiments include those wherein collection vessel 20 is removable from airflow separator 15, such as by screw on/off threads, by interference fit, or removable bolts, to name some of the possible ways of gaining access to sample in the collection vessel.

As selectively chosen by a user, a variety of different sensors types may be utilized for the purpose of determining the amount (mass, volume and/or concentration) of the bulk material sampled. These sensors may operate on a number of principles including, but not limited to, weight, density, optical properties (density, adsorption or transmission), electrical properties (conductance, impedance, inductance, capacitance, charge, resistance, etc.), radio frequency, ultrasonic, laser, electrochemical, chemical or biological. These sensors may be constructed using traditional approaches or using MEMS/nanotechnology methods. Sensing can be achieved using one or multiple sensors of the same or different type including mixed-mode approaches. Sensors can be either analog or digital in nature. The scope of present embodiments is not limited by the type of sensor or the number of sensors.

In some embodiments, processor 35 includes one or more general or special purpose microprocessors, or any one or more processors of any kind of digital computer, including ones that sense conditions, such as the level of the sampled material in the collection vessel, and which perform various steps based on evolving conditions as further discussed herein. Processor 35 further includes, or is communicatively coupled to, computer readable storage medium such as, for example memory, which may optionally include read-only memory (ROM), random access memory (RAM), non-volatile RAM (NVRAM), optical media, magnetic media, semiconductor memory devices, flash memory devices, mass data storage device (e.g., a hard drive, CD-ROM and/or DVD units) and/or other storage as is known in the art. Additionally, processor 35 includes, or is communicatively coupled to, memory having computer readable and executable, machine-readable program instructions, rules, and/or routines (any set of which may be referred to herein generally as "Instructions") which, when executed by processor 35, cause it to perform the steps as described herein. Accordingly, processor 35 stores Instructions in memory and executes the Instructions, including for an algorithm as described with FIG. 3 that determines how valve modulation is actuated, with actuation occurring according to techniques commonly known and practiced. Processor 35 can be a microcontroller.

Various alternative forms of memory as known in the art can be used for storage. The memory storage associated with processor 35 can include local storage (e.g., microSD memory card) for later retrieval of data associated with a particular sampling run, and Instructions can be configured to switch into and out of sleep mode between sampling runs to save power. In some embodiments, processor 35 is coupled to complementary components (not shown), for example user interface screens, key pads, touch pads and the like which are responsive to operator input to allow user control of the system, as well as to components like audible indicators, and/or light indicators.

It will be understood that the embodiments described herein are not limited in their application to the details of the teachings and descriptions set forth, or as illustrated in the accompanying figures. Rather, it will be understood that the present embodiments and alternatives, as described and claimed herein, are capable of being practiced or carried out in various ways. Also, it is to be understood that words and phrases used herein are for the purpose of description and should not be regarded as limiting. The use herein of such words and phrases as "including," "such as," "comprising," "e.g.," "containing," or "having" and variations of those words is meant to encompass the items listed thereafter, and equivalents of those, as well as additional items.

Accordingly, the foregoing descriptions of several embodiments and alternatives are meant to illustrate, rather than to serve as limits on the scope of what has been disclosed herein. The descriptions herein, including the Figures, are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. A material sample separation and collection system, comprising:
    at least one airflow separator, having an airflow separator inlet and an airflow separator outlet;
    a conduit providing fluid communication between the airflow separator and a sampling point, and thereby defining a path for sampled material being transported from the sampling point, the conduit further comprising a conduit inlet;

a collection vessel that receives sampled material from the sampling point;

one or more valves drawing airflow into the conduit located between the conduit inlet and the collection vessel;

one or more sensors that sense a level of the sampled material in the collection vessel; and a processor that tracks a duration of time needed to fill at least a defined portion of the collection vessel with sampled material, and executes machine readable program instructions to modulate the position of one or more valves;

wherein a volume of sampled material collected over time is variable by modulating the position of said one or more valves.

2. The material sample separation and collection system of claim 1, wherein one or more valves is positioned along the conduit.

3. The material sample separation and collection system of claim 1, wherein one or more valves is upstream of the airflow separator.

4. The material sample separation and collection system of claim 1, wherein the amount of sampled material collected over time determines a sampling rate, and the sampling rate is modulated automatically based on real time data from one or more sensors.

5. The material sample separation and collection system of claim 1, further comprising a fan positioned at the airflow separator outlet for generating a force that produces an airflow that draws an air stream into the conduit via the conduit inlet, wherein the force producing the airflow is constant.

6. The material sample separation and collection system of claim 1, wherein the sample contains bulk materials.

7. The material sample separation and collection system of claim 6, wherein the airflow separator is configured to receive a carrier fluid, and a collected sample encounters the carrier fluid within the airflow separator and is urged into the collection vessel by the carrier fluid.

8. The material sample separation and collection system of claim 1, wherein opening one or more valves reduces the rate of sample collection.

9. A method for collecting a sample, comprising:

providing a material sample separation and collection system according to claim 1;

monitoring a collection fill rate based on an amount of sampled material entering the collection vessel over a unit of time;

comparing sample time to the collection fill rate; and adjusting a material sampling rate by modulating a position of said one or more valves.

10. The method of claim 9, wherein monitoring a collection fill rate occurs while the collection vessel is partially full.

11. The method of claim 10, wherein the modulation of one or more valves occurs automatically based on real time data from one or more sensors.

12. The method of claim 9, wherein modulating the position of one or more valves includes opening one or more valves to reduce the material sampling rate.

\* \* \* \* \*